(12) United States Patent
Barrere et al.

(10) Patent No.: US 6,180,392 B1
(45) Date of Patent: Jan. 30, 2001

(54) STREPTOMYCES STRAINS AND PROCESS TO PRODUCE SINGLE STREPTOGRAMIN COMPONENT

(75) Inventors: Geneviève Barrere, Paris; Catherine Jumel, Escalquens; Patricia Lacroix, Bry-sur-Marne; Corinne Lehmann, Sainte-Geneviève-des-Bois; Alain Sabatier, Paris, all of (FR)

(73) Assignee: Aventis Pharma S.A., Antony (FR)

( * ) Notice: Under 35 U.S.C. 154(b), the term of this patent shall be extended for 0 days.

(21) Appl. No.: 08/307,796

(22) PCT Filed: Mar. 31, 1993

(86) PCT No.: PCT/FR93/00324

§ 371 Date: Nov. 10, 1994

§ 102(e) Date: Nov. 10, 1994

(87) PCT Pub. No.: WO93/20182

PCT Pub. Date: Oct. 14, 1993

(30) Foreign Application Priority Data

Apr. 1, 1992 (FR) .................................................. 92 03939

(51) Int. Cl.$^7$ ..................................................... C12N 1/20
(52) U.S. Cl. ..................... 435/253.5; 435/440; 435/71.2; 435/71.3
(58) Field of Search ............... 435/71.3, 252.1, 435/254.1, 440, 253.5, 71.2

(56) References Cited

U.S. PATENT DOCUMENTS

| | | | |
|---|---|---|---|
| 3,137,640 | * 6/1964 | Watanabe | 435/253.5 |
| 4,355,112 | 10/1982 | Okumura et al. | 435/253 |
| 4,536,397 | * 8/1985 | Okumura | 514/11 |

FOREIGN PATENT DOCUMENTS 0 248 703   12/1987   (EP) .

OTHER PUBLICATIONS

Biotechnology Abstracts—Derwent Abstract No. 84–07062 "Selective production of antibiotic neoviridogrisein II—using propylhydroxylase deficient *Streptomyces sp.* strain obtained by chemical or radiation mutagenesis" & JP –A–59059198 (Sanraku–Ocean) Apr. 4, 1984.

Folia Microbiologica, vol. 35, No. 6, 1990, p. 494, Prague, Tchecoslovaquie, M. Blumauerova et al.: Physiological and genetic aspects of virginiamycin production.

Database WPI, week 6800, Derwent Publications Ltd., AN 66–10866F, FR –A–1349946 (Kanegafuchi Chem Ind Co Ltd), 1963.

The Journal of Antibiotics Series A, vol. XIII, No. 1, Jan. 1960, pp., 62–69, K. Watanabe: Studies on mikamycin. V in vitro synergistic action and differential assay of mikamycin components.

Biotechnology of Industrial Antibiotics, vol. 22, 1984, pp. 695–720, A.M. Biot: Virginiamycin: properties, biosynthesis, and fermentation.

Nagato et al, *Agric. Biol. Chem.* vol. 48, 1984, p. 3041–45.*
Okumura et al, *Agric Biol Chem*, vol. 47, 1983, p. 1087–1092.*
Rezanka et al., *Folia Microbiol.*, 37(2), 105–110, 1992.*

* cited by examiner

*Primary Examiner*—Irene Marx
(74) *Attorney, Agent, or Firm*—Finnegan, Henderson, Farabow, Garrett, Dunner, L.L.P.

(57) ABSTRACT

This invention relates to micro-organisms capable of selectively producing streptogramin components A and B, the preparation of said micro-organisms, and streptogramin A or B.

5 Claims, 2 Drawing Sheets

STREPTOMYCES STRAINS AND PROCESS TO PRODUCE SINGLE STREPTOGRAMIN COMPONENT

This application was filed under 35 USC 371 as the national phase of PCT/FR93/00324 filed Mar. 31, 1993.

FIELD OF THE INVENTION

The present invention relates to new microorganisms, to a method for preparing them and also to their use. More especially, the invention relates to microorganisms that produce antibiotics.

BACKGROUND OF THE INVENTION

Of the many antibiotics described in the prior art, some possess the feature of consisting of several active components acting together synergistically. This is the case, in particular, with the antibiotics of the streptogramin family, which are composed of a macrolactone (group A component) and a depsipeptide (group B component). The antimicrobial activity and the mode of action of these antibiotics have been the subject of studies, in particular by Tanaka (Antibiotics, vol. III p. 487, Springer, Berlin (1975)) and Vasquez (Antibiotics, vol. III p. 521, Springer, Berlin (1975)). The general structure of the molecules of groups A and B is shown in FIGS. 1 and 2.

Among the known antibiotics of the streptogramin family, there may be mentioned, more especially:

pristinamycins, mikamycins, virginiamycins, vernamycins, ostreogrycins, synergistins, plauracins, etamycins, streptogramins, viridogriseins, griseoviridins, or neoviridogriseins.

The active form of each of these antibiotics consists of a synergistic combination of molecules belonging to group A as shown in FIG. 1 and molecules belonging to group B as shown in FIG. 2, or of related molecules.

Related molecules are understood, in the sense used in the present invention, to mean molecules possessing the general skeleton of those shown in FIGS. 1 and 2 but which may differ from the latter by substitutions or other secondary variations, and possessing an activity of the same nature.

The antibiotics of the streptogramin family are produced by a wide variety of microorganisms, and especially by bacteria of the genus Actinomycete and by certain fungi. These microorganisms are characterised in that they synthesise both components A and B simultaneously.

Table 1 lists the main productive microorganisms, together with the corresponding antibiotics.

Studies have been carried out with the object of increasing the levels of production of these microorganisms. There may be mentioned, in particular, the works of Biot (Biotechnology of Industrial Antibiotics, vol. 22 (1984) p. 695) or of Prikrylova et al. (Biotechnology and Bioindustry/2 (1988) 20) concerning improvement in the culture conditions and the effect of mutagenic agents on the levels of production of virginiamycin by *S. virginiae*. As the authors state, the overproductive mutants obtained always produce components A and B simultaneously.

However, the fact that the streptogramin-producing microorganisms which are available in the prior art synthesise both synergistic components A and B of the antibiotic simultaneously, in the same fermentation medium, constitutes a considerable drawback in some cases.

In effect, to optimise the use of these antibiotics and to be able to use them as pharmaceutical agents, it is preferable to be able to separate and purify the A and B components of the streptogramins. This is also essential in order to be able to carry out chemical studies on streptogramins, especially with the object of preparing semisynthetic derivatives such as, for example, those described in Patents FR 2,549,063, FR 2,549,065, EP 191,662 or EP 248,703.

However, accessibility to these different components is difficult as a result, in particular, of their simultaneous production and of the similarity of their physicochemical properties. Furthermore, these microorganisms generally synthesise several different molecules of each component, leading to a mixture of many compounds, in highly variable proportions, in the fermentation must. In effect, many molecules belonging to groups A and B of streptogramins, possessing very different biological activities and which are produced simultaneously by the microorganisms, are known at the present time. Thus, the following molecules belonging to group A are known in the prior art: pristinamycins PIIA and PIIB, virginiamycins M1 and M2, mikamycin A or ostreogrycins A and G. Likewise, the following molecules belonging to group B are known in the prior art: pristinamycins PIA, PIB and PIC, virginiamycins S1, S2, S3, S4 and S5, mikamycin B, vernamycins Bα, Bβ, Bγ and Bδ, ostreogrycin B, B1, B2 and B3 or neoviridogriseins I, II, III and IV.

For these reasons, it is difficult to obtain active and pharmaceutically acceptable synergistic mixtures of streptogramins satisfactorily at industrial level. It is also difficult to carry out chemical studies on streptogramins (structure-function relationship, development of water-soluble forms, and the like). The present invention enables the drawbacks of the prior art in this field to be remedied.

SUMMARY OF THE INVENTION

The Applicant has now shown that it is possible to obtain microorganisms that produce components A and B of streptogramins separately in a stable manner. The Applicant has hence developed, and this constitutes a subject of the present invention, microorganisms capable of selectively producing components A and B of streptogramins. The invention relates both to microorganisms capable of selectively producing molecules of group A of streptogramins or molecules of group B of streptogramins, and to microorganisms capable of selectively producing a molecule specific to one of these groups.

The invention thus makes possible the separate production of streptogramin A or B in large quantities.

The invention also makes it possible to use methods for purification of streptogramins which are simpler and hence more efficacious and more economical, since there are no longer, or are fewer, interactions between the different components during the extraction.

The invention also makes it possible to vary the respective quantities of components A and B in a mixture, and hence to produce antibiotic compositions which are optimal in respect of both purity and synergistic efficiency.

The invention also makes it possible to obtain products in sufficient quantity and purity to carry out chemical studies in order to improve further the properties of streptogramins.

The invention thus provides a system for production of streptogramins that permits a much more efficacious industrial exploitation of these antibiotics.

More especially, the invention relates to microorganisms capable of selectively producing components A and B of streptogramins chosen from the group comprising pristinamycin, virginiamycin, mikamycin, ostreogrycin, synergistin, viridogrisein, vernamycin, plauracin, etamycin, griseoviridin, neoviridogrisein and streptogramin.

BRIEF DESCRIPTION OF DRAWINGS

In a preferred embodiment, the invention relates to microorganisms capable of selectively producing the components A of streptogramins corresponding to the general formula shown in FIG. 1, in which:

Y represents a D-proline, a 4,5-dehydroproline, a D-alanine or a D-cysteine,

R0 represents a C=O or CHOH group,

R1 is a hydrogen atom or a methyl group,

R2 is a hydrogen atom or a methyl group, and

R3 is a methyl or isopropyl group.

Figure 2A:
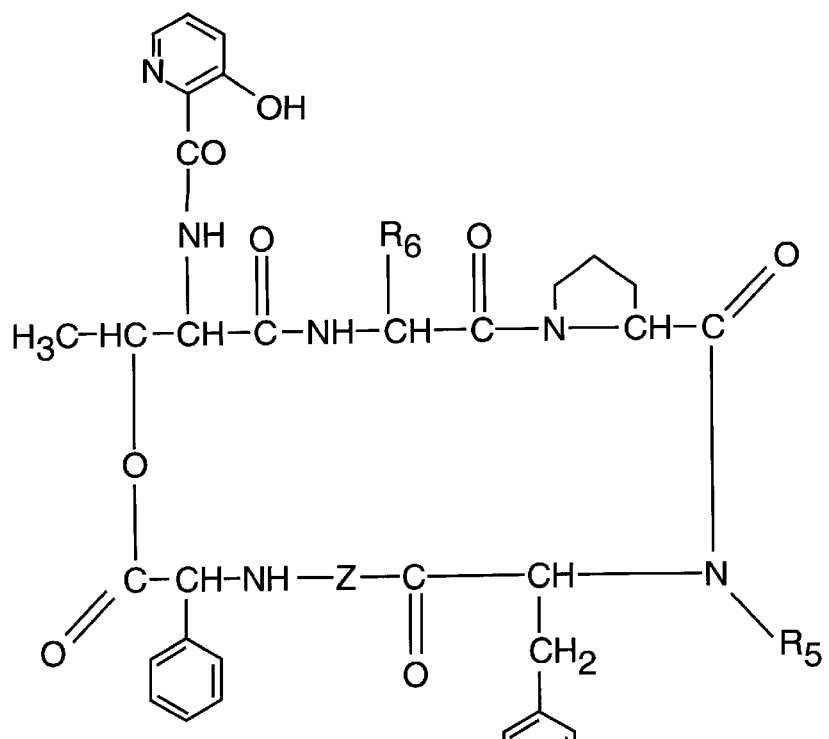

In another preferred embodiment, the invention relates to microorganisms capable of selectively producing the components B of streptogramins corresponding to the general formula shown in FIG. 2(a), in which:

Z represents an L-proline, an L-aspartic acid, a pipecolic acid, a 4-oxopipecolic acid, a 4-hydroxy-L-pipecolic acid or a 5-hydroxy-4-oxo-L-pipecolic acid, R4 is a hydrogen atom or an amine of formula NH(CH3) or N(CH3)2, R5 is a hydrogen atom or a methyl group, and R6 is a methyl or ethyl group.

Figure 2B:
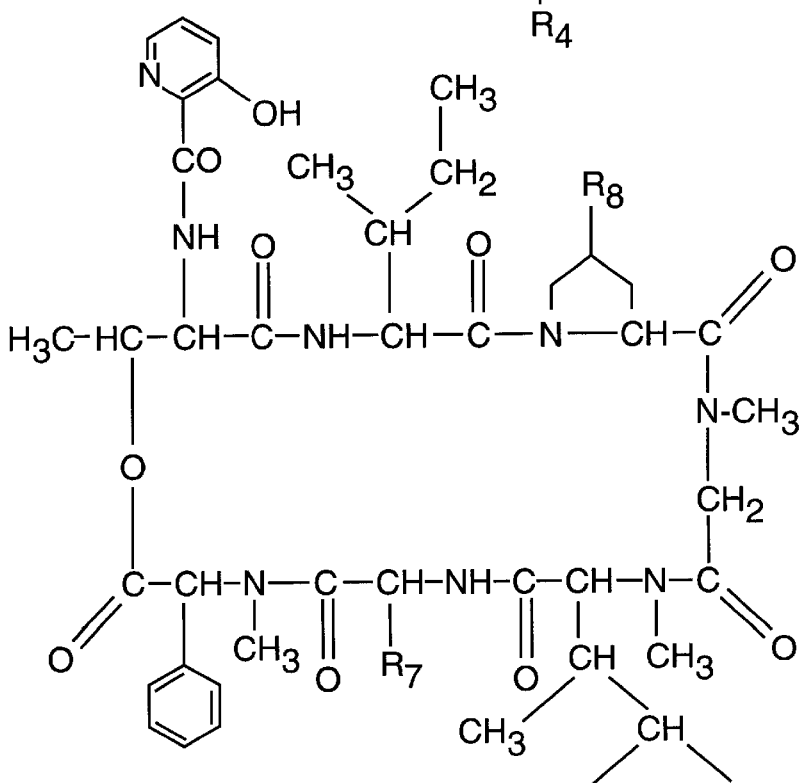

Still in a preferred embodiment, the invention relates to microorganisms capable of selectively producing the components B of streptogramins corresponding to the general formula shown in FIG. 2(b), in which:

R7 represents a hydrogen atom or a hydroxyl group, and

R8 represents a methyl or ethyl group.

More preferably, the invention relates to microorganisms capable of selectively producing, alone or mixed, components A or B of streptogramins chosen from the group comprising pristinamycin, virginiamycin, ostreogrycin and mikamycin.

Figure 1:
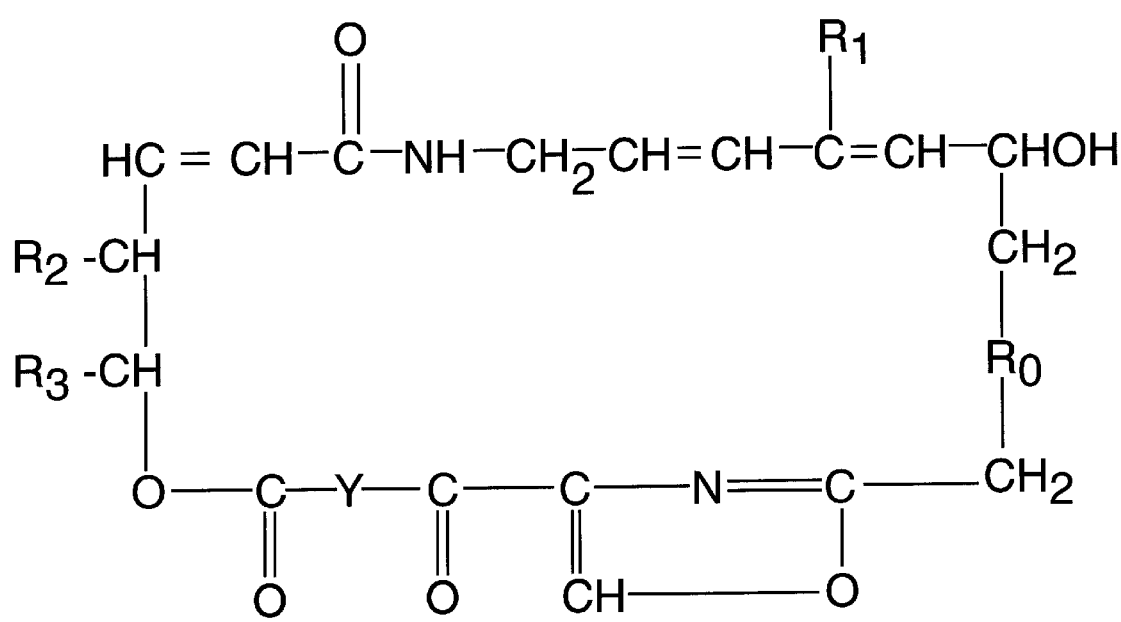

As an example, the invention relates to microorganisms capable of selectively producing the components A of streptogramins corresponding to the general formula presented in FIG. 1, in which R0 represents a C=O group, R1 represents a methyl group, R2 represents a methyl group, R3 represents an isopropyl group and Y represents a D-proline or a 4,5-dehydroproline; and microorganisms capable of selectively producing the components B of streptogramins corresponding to the general formula presented in FIG. 2(a), in which:

R4 is an amine of formula N(CH3)2, R5 is a methyl group, R6 is an ethyl group and Z represents a 4-oxopipecolic acid; or R4 is an amine of formula NHCH3, R5 is a methyl group, R6 is an ethyl group and Z represents a 4-oxopipecolic acid; or R4 is an amine of formula N(CH3)2, R5 is a methyl group, R6 is a methyl group and Z represents a 4-oxopipecolic acid; or R4 is an amine of formula N(CH3)2, R5 is a methyl group, R6 is an ethyl group and Z represents a 5-hydroxy-4-oxo-L-pipecolic acid; or R4 is a hydrogen atom, R5 is a methyl group, R6 is an ethyl group and Z represents a 4-oxopipecolic acid; or R4 is a hydrogen atom, R5 is a methyl group, R6 is a methyl group and Z represents a 4-oxopipecolic acid; or R4 is a hydrogen atom, R5 is a methyl group, R6 is an ethyl group and Z represents a 5-hydroxy-4-oxo-L-pipecolic acid; or R4 is a hydrogen atom, R5 is a hydrogen atom, R6 is an ethyl group and Z represents a 4-hydroxy-L-pipecolic acid.

Preferably, the microorganisms of the invention are essentially bacteria of the genus Actinomycete or fungi.

Still more preferably, the microorganisms of the invention belong to the genus Streptomyces.

The microorganisms of the invention may be cultured under standard aerobic fermentation conditions. In particular, the nutrient medium generally consists of a carbon source, a nitrogen source and mineral salts. As a carbon source, sugars, oils, organic acids, dextrin, starches, glycerol, and the like, may be used in particular. As a nitrogen source, there may be mentioned amino acids, extracts (malt, soya bean, cotton seed, tomato, maize, and the like), and plant meal, viscera, miscellaneous hydrolysates (casein, yeast, and the like) and industrial byproducts such as "distillers solubles". As a mineral source, it is possible to use sodium, potassium, ammonium or calcium chlorides, nitrates, carbonates, sulphates and phosphates, or trace elements such as magnesium, iron, copper, zinc, manganese or cobalt.

The microorganisms of the present invention are preferably obtained from microorganisms that are non-selective producers of streptogramins.

Non-selective microorganisms are understood, in the sense used in the present invention, to mean microorganisms which synthesize components A and B of streptogramins simultaneously. All the microorganisms listed in Table 1 constitute non-selective microorganisms in the sense used in the invention. The Applicant has now shown that microorganisms that are selective producers of streptogramins may be obtained from non-selective microorganisms that produce streptogramins. To this end, a novel process has been developed, involving a first, optional step of mutagenesis followed by a selection step.

Another subject of the present invention hence relates to a method for preparing the microorganisms defined above, according to which the following steps are carried out:

in a first, optional step, a mutagenesis is performed on a microorganism that is a non-selective producer of streptogramins, and in a second step, the selective microorganisms are selected.

As stated above, the non-selective microorganisms generally belong to the group comprising Actinomycetes and fungi. More preferably, the starting microorganisms which can be used in the method of the invention are microorganisms that are non-selective producers of a streptogramin chosen from the group comprising pristinamycin, virginiamycin, mikamycin, ostreogrycin, synergistin, viridogrisein, vernamycin, plauracin, etamycin, neoviridogrisein, griseoviridin and streptogramin. As an example, the microorganisms listed in Table 1 constitute non-selective microorganisms which can be used in the method of the invention. Still more preferably, the method of the invention is carried out using microorganisms chosen from *Streptomyces alborectus, Streptomyces diastaticus,*

*Streptomyces graminofaciens, Streptomyces griseus, Streptomyces loidensis, Streptomyces mitakaensis, Streptomyces olivaceus, Streptomyces ostreogriseus, Streptomyces pristinaespiralis, Streptomyces virginiae, Streptomyces lavendulae, Streptomyces griseoviridus,* Micromonospora sp., *Actinomyces auranticolor, Actinomyces daghestanicus* and *Actinomyces azureus.*

Still more preferably, the method of the invention is carried out using microorganisms chosen from *Streptomyces alborectus, Streptomyces mitakaensis, Streptomyces pristinaespiralis, Streptomyces ostreogriseus* and *Streptomyces virginiae.*

The first step of the method consists in modifying the non-selective microorganism so as to increase its overall capacity for production of antibiotic, and/or so that it synthesises only one of the 2 components of streptogramins. This may be obtained by genetic modifications (mutation at structural genes for enzymes involved in the pathway of biosynthesis, or at sequences permitting the expression of such structural genes, for example) or biochemical modifications (modification of a post-translational mechanism, alteration of a feedback-inhibition mechanism, and the like). To this end, various tools of mutagenesis may be used, and in particular:

physical agents: X-rays, ultraviolet rays; or
  chemical agents such as:
    alkylating agents such as ethyl methanesulphonate (EMS), N-methyl-N'-nitro-N-nitrosoguanidine (Delic et al. Mutation Res. 9 (1970) 167–182) or 4-nitroquinoline 1-oxide (NQO);
    bialkylating agents;
    intercalating agents; or
  any system of mutational insertion into DNA, and especially transposons, integrative plasmids, phages or prophages; or alternatively
  protoplast fusion (Cohen, Nature 268 (1977) 171–174).

Each of these tools may be applied to the non-selective microorganisms in the state of spores or of spores which have germinated or are in the course of germination, or to mycelium. Moreover, these various tools may also be used in combination.

Although some preferred mutational schemes may be set out, leading to the formation of the desired selective microorganisms, it is understood that the mutagenesis step may be adapted by a person skilled in the art in accordance with the starting microorganism used, the streptogramin desired and the objectives set (increase in the rate of synthesis of the desired component, increase in the level of production of the latter, reduction in the consumption of starting materials by the microorganism, and the like). Under these conditions, the present invention is not limited to a precise mutational scheme, but extends to all manipulations (random or directed) that enable microorganisms capable of selectively producing one component of streptogramins from non-selective microorganisms to be obtained.

As a specific example, mutagenesis in the presence of ethyl methanesulphonate or by treatment with UV gives good results.

As regards the second step of the method, this enables the selective microorganisms to be identified and isolated. This step may be carried out in different ways, and in particular by means of a sensitivity test with respect to a microbe. To this end, different microbes specifically sensitive to the components of group A or to those of group B of streptogramins exist. There may be mentioned, in particular, the *Bacillus subtilis* (ATCC6633), *Bacillus circulans, Bacillus cereus* (Watanabe, J. Antibio, Ser. A XIII(1) (1960) 62) or *C. xerosis* (Watanabe, loc. cit.), which are specifically sensitive to the components of group B. There may also be mentioned *Streptococcus agalactiae* B96 (Antimicrob. Agents Chemother. 10(5) (1976) 795), *Micrococcus luteus* (Prikrylova, loc. cit.) or *Sarcina lutea* (ATCC9341), which are specifically sensitive to the components of group A. Moreover, it is also possible to prepare artificially microbes that are specifically sensitive to one component of streptogramins, by inserting a gene for resistance to one of the components of streptogramins into a microbe that is sensitive to both components. Some of these genes have, in effect, been cloned (Le Goffic et al., J. Antibio. XXX(8) (1977) 665; Le Goffic et al., Ann. Microbiol. Inst. Pasteur 128B (1977) 471; Solh et al., Path. Biol. 32(5) (1984) 362), and a person skilled in the art can introduce such genes into different microbes using standard techniques of molecular biology. The selection step may also be performed by an ELISA test using antibodies specific for components A or B, or alternatively by analytical techniques such as chromatography (liquid chromatography, thin-layer chromatography, and the like). In the case of a sensitivity test with respect to a microbe, it is, in addition, preferable to validate the selection by chromatographic assay.

Another subject of the present invention relates to a method for preparing one of the components A or B of streptogramins, characterised in that a microorganism as defined above is cultured under production conditions, and the component produced is separated from the culture medium. Components A and B of streptogramins may be separated from the fermentation must by standard methods of solvent extraction. It is, in particular, possible to work according to the following protocol: filtration of the must after acidification to approximately pH 3, neutralization of the filtrate to pH 7, extraction with dichloroethane, concentration and precipitation of the component produced by a poor solvent such as petroleum ether. The component thereby obtained can then be purified according to known methods such as chromatography. Methods of purification of streptogramins from fermentation must of non-selective microorganisms have been described in the literature, and may be applied to the present invention (see, in particular, Chapin et al., J. of Liquid Chromatography 11(11) (1988) 2367; Prikrylova et al., Biotechnology and Bioindustry/2 (1988) 20; Biot A. Biotechnology of Industrial Antibiotics, vol. 22 (1984) p. 695).

In a particular embodiment, the invention relates to a method for preparing a macrolactone of the general formula shown in FIG. 1, in which the different substituents are defined as above, or a mixture of such macrolactones, characterized in that a specific microorganism as defined above is cultured, and the products obtained are separated from the culture medium.

In another embodiment, the invention relates to a method for preparing a depsipeptide of the general formula shown in FIG. 2(*a*), in which the different substituents are defined as above, or a mixture of such depsipeptides, characterized in that a specific microorganism as defined above is cultured, and the products obtained are separated from the culture medium.

DESCRIPTION OF THE DRAWINGS

FIG. 1 shows the general structure of molecules of group A (macrolactone) of the streptogramin family.

FIG. 2 shows the general structure of molecules of group B (depsipeptide) of the streptogramin family.

DETAILED DESCRIPTION OF THE INVENTION

The subject of the invention is also any component A of a streptogramin, when it is obtained from the culture medium of a selectively productive microorganism according to the invention. Preferably, the component is a macrolactone of the general formula shown in FIG. 1, in which the different substituents are defined as above, or a mixture of such macrolactones.

The subject of the invention is also any component B of a streptogramin, when it is obtained from the culture medium of a selectively productive microorganism according to the invention. Preferably, the component is a depsipeptide of the general formula shown in FIG. 2, in which the different substituents are defined as above, or a mixture of such depsipeptides.

The components A and B of streptogramins thereby obtained (from the culture medium of selective microorganisms according to the invention) can be used for structure-function studies, for the production of semisynthetic derivatives or for the preparation of antibiotic compositions.

The present invention will be described more completely by means of the examples which follow, which are to be considered as illustrative and non-limiting.

EXAMPLES

Example 1

Preparation of microorganisms that are specific producers of pristinamycin PII from the strain DS5647

This example was carried out without a prior step of mutagenesis.

1. Selection by sensitivity to a microbe.

A suspension of *S. pristinaespiralis* DS5647 (ATCC25486) spores is plated out after dilution on complete agar medium (HT medium: white dextrin 10 g; N-Z-amine type A 2 g; yeast extract 1 g; meat extract 1 g; CoC12.6H2O 0.02 g; bacto agar 20 g; demineralized water q.s. 1 l: see Pridham, Antibiotic Annual (1956) 957) so as to have isolated colonies. After a growth step, these isolated colonies are subcultured on production medium (HT medium). At a defined age, plugs are withdrawn from the medium in order to assay the pristinamycins produced.

1.1. Assay of pristinamycins PI.

A portion of the plugs withdrawn is deposited on agar medium [25 g/l of Merieux medium No. 2 (Merieux 5 177 1), 20 g/l of NaCl, 5 g/l of TAPS buffer, pH 8.5] with the addition of 40 mg/l of pristinamycin PII and which is inoculated with $3.6 \times 10^8$ sp/l of *Bacillus subtilis* ATCC6633. This medium is prepared in the following manner on the day the plugs are withdrawn: the agar medium, distributed in 200-ml Erlenmeyers, is melted using microwaves, and the temperature of the flask contents is then brought down to approximately 50° C. in a water bath and then monitored under a hood with a thermometer dipping into the medium while stirring gently. When a temperature of 48° C. is reached, the following are added to the contents of each flask:

2 ml of a solution of pristinamycin PII at a concentration of 4 mg/ml (final concentration 40 mg/l), and 0.4 ml of a suspension of *Bacillus subtilis* ATCC6633 at a concentration of $3.6 \times 10^9$ sp/ml, diluted twenty-fold (final concentration $3.6 \times 10^8$ sp/l).

The medium is homogenized by gentle stirring, and then poured in the proportion of the contents of one flask per plate (NUNC "Screening Plate") on an absolutely level surface.

After deposition of the plugs on the plates (diameter of the plug borer: 4.0 mm), a prediffusion of 6 hours at 4° C. is performed, and the plates are then incubated for 16 hours at 37° C.

1.2. Assay of pristinamycins PII.

A portion of the plugs withdrawn is deposited on agar medium [52 g/l of Brain Heart infusion agar] with the addition of 10 mg/l of pristinamycin PI and which is inoculated with $5 \times 10^8$ sp/l of *Streptococcus agalactiae* B96. This medium is prepared in the following manner on the day the plugs are withdrawn: the agar medium, distributed in 200-ml Erlenmeyers, is melted using microwaves, and the temperature of the flask contents is brought down to approximately 50° C. in a water bath and then monitored under a hood with a thermometer dipping into the medium while stirring gently. When a temperature of 45° C. has been reached, the following are added to the contents of each flask:

1 ml of a solution of pristinamycin PI at a concentration of 2 mg/ml (final concentration 10 mg/l), and 0.7 ml of a suspension of *Streptococcus agalactiae* B96 at a concentration of $5 \times 10^8$ sp/ml.

The medium is homogenized by gentle stirring, and then poured in the proportion of the contents of one flask per plate (NUNC "Screening Plate") on an absolutely level surface.

After deposition of the plugs on the plates (diameter of the plug borer: 3.5 mm), a prediffusion of 6 hours at 4° C. is performed, and the plates are then incubated for 16 hours at 37° C.

1.3. Results

The diameters of the inhibition halos are measured for each of the plates containing the test microbes. They are dependent on the concentration of antibiotic (component A or B) present in the medium, and hence enable the clones that do not produce one or other of the components to be identified.

Of 3600 clones tested, 36 not producing pristinamycin PI were identified in this way.

2. Selection by chromatographic assay.

The clones thus identified not producing pristinamycin PI but producing pristinamycin PII in a solid medium were then tested in a liquid medium. For this purpose, 0.5 ml of a suspension of spores of the strains selected in 1. is added under sterile conditions to 40 ml of inoculum medium in a 300-ml Erlenmeyer. The inoculum medium consists of 10 g/l of corn steep, 15 g/l of sucrose, 10 g/l of (NH4)2SO4, 1 g/l of K2HPO4, 3 g/l of NaCl, 0.2 g/l of MgSO4.7H2O and 1.25 g/l of CaCO3. The pH is adjusted to 6.9 with sodium hydroxide before introduction of the calcium carbonate. the Erlenmeyers are stirred for 44 hours at 27° C. on a rotary stirrer at a speed of 325 rpm. 2.5 ml of the above culture 44 hours old are added under sterile conditions to 30 ml of production medium in a 300-ml Erlenmeyer. The production medium consists of 25 g/l of soya bean meal, 7.5 g/l of starch, 22.5 g/l of glucose, 3.5 g/l of seeding yeast, 0.5 g/l of zinc sulphate and 6 g/l of calcium carbonate. The pH is adjusted to 6 with hydrochloric acid before addition of the calcium carbonate. The Erlenmeyers are stirred for 24 h, 27 h or 30 h. 10 g of must are then weighed into a smooth Erlenmeyer, to which amount 20 ml of mobile phase composed of 62.5% of acetonitrile and 37.5% of a 0.1 M solution of concentrated K2HPO4 are added. After stirring on a stirrer (325 rpm) for 20 minutes at room temperature, the mixture is filtered through filter paper and the pristinamycin contained in the filtrate is assayed by LC. For this purpose, 2.4 ml of the filtrate are dissolved in a diluent composed of acetonitrile and water in a 30:70 ratio. This solution is injected onto an SFCC column (length: 25 cm; diameter: ¼ inch; stationary phase: Nucleosil C8 5 microns). The mobile phase is composed of 630 ml of 0.1 M KH2PO4 (adjusted to pH 3 with H3PO4) and 370 ml of acetonitrile, and elution is performed at a flow rate of 1 ml/minute. The streptogramins are detected by measuring absorption at 206 nm with an LDC Spectromonitor III detector.

This analysis enables 3 clones that are selective producers of pristinamycin PII to be demonstrated among the 36 identified above. The clone Pr4R12 was deposited on Mar. 11, 1992 at the Centraalbureau voor Schimmelcultures in Baarn (Holland), according to the conditions of the Budapest Treaty, under number CBS 183.92.

Example 2

Preparation of microorganisms that are specific producers of pristinamycin PI from the strain DS5647

This example comprises a step of mutagenesis on the non-selective microorganism, followed by a selection step.

1. Mutagenesis.

1.1. Mutagenesis with ethyl methanesulphonate (EMS).

A first type of mutagenesis was carried out on the non-selective strain DS5647 using a chemical agent, namely ethyl methanesulphonate (EMS), as a mutagenic agent.

A suspension of spores of the strain DS5647 is taken up in 40 ml of 0.2 M phosphate buffer, pH 7 (0.2 M K2HPO4; pH adjusted to 7 with 0.2 M KH2PO4 solution). This suspension is then distributed in 4 100-ml Erlenmeyers in the proportion of 10 ml per Erlenmeyer, equivalent to approximately $6 \times 10^8$ spores/Erlenmeyer. 0.4 ml of EMS is then added into each Erlenmeyer (final concentration 4%), and the suspensions are stirred at 280 rpm and at 30° C. for variable times (see table). The suspensions are then transferred to large 250-ml pots, and 90 ml of 0.16 M Na2S3O3.5H2O solution are added. A 0.5 ml sample is removed from each pot and plated out on a dish containing HT medium to determine the degree of survival by counting relative to the control (see table). The remainder of the suspension is centrifuged, rinsed once with 10 ml of 0.16 M Na2S3O3.5H2O, centrifuged again and then taken up with 10 ml of Hirsch medium (J. Bacteriol. 126 (1976) 13). After phenotypic expression overnight at 30° C. with stirring (280 rpm), the cells are plated out on a dish containing HT medium to determine the degree of auxotrophy and the morphological heterogeneity of the colonies. To measure the degree of auxotrophy, the colonies are subcultured on minimum medium and the % of colonies incapable of growth is determined. The minimum medium is composed of agar 10 g; L-asparagin 0.5 g; K2HPO4 0.5 g; MgSO4.7H2O 0.2 g; FeSO4.7H2O 0.01 g; autoclaved glucose 10 g; distilled water 1 l (Hopwood D. A., Bact. Rev. 31 (1967) 373). The results obtained are presented in the following table:

| Parameters | R0 | R1 | R2 | R3 |
|---|---|---|---|---|
| EMS | 0 | 4% | 4% | 4% |
| Stirring time | 150 min | 130 min | 150 min | 180 min |
| % survival | 100 | 5.7 | 0.94 | 0.21 |
| % of auxotrophs | 0.4 | 4.3 | 6.0 | 5.8 |
| Heterogeneity | +/− | + | +++ | +++ |

1.2. Mutagenesis with UV.

A second type of mutagenesis was carried out on the non-selective strain DS5647 using a physical agent, namely ultraviolet rays, as a mutagenic agent.

A suspension of spores of the strain DS5647 ($7 \times 10^8$ spores/ml) is diluted with water containing 0.01% Tween (final concentration: $5 \times 10^7$ spores/ml). This suspension is distributed in Petri dishes in the proportion of 10 ml per dish, equivalent to approximately $5 \times 10^8$ spores/dish. The dishes are then exposed to UV at different irradiation powers (see table). The contents of each dish are then centrifuged for 10 minutes at 3000 rpm, and the pellets are taken up with 5 ml of Hirsch medium. The cells are maintained at 30° C. on a stirrer until it is observed that germination is beginning. The cells are then plated out, and the following parameters are determined as evidence of the efficiency of the mutagenesis: degree of survival and degree of auxotrophy. These parameters are determined as in the example above.

| Parameters | T0 | T1 | T2 | T3 | T4 | T5 | T6 |
|---|---|---|---|---|---|---|---|
| Power of irradiation ergs/mm² | 0 | 3420 | 4050 | 5940 | 7200 | 8100 | 9120 |
| Surviving cells/ml | $10^7$ | $10^4$ | $10^3$ | $3 \times 10^2$ | $10^2$ | $4 \times 10^2$ | $10^2$ |
| % Survival |  | 0.1 | 0.01 | 0.003 | 0.001 | 0.004 | 0.001 |
| % of auxotrophs | <0.4 | 0.4 | 3.2 | 2.8 | 5.6 | 2.8 | 3.8 |

2. Selection of specific producers of pristinamycin PI.

The selection is performed as in Example 1 in two steps (test of sensitivity to a microbe in a solid medium, and validation in a liquid medium by chromatographic analysis) from the colonies obtained by EMS mutagenesis (R2). Of 3600 initial clones, 6 were identified in a solid medium, 3 of which were confirmed in a liquid medium as specific producers of pristinamycin PI. The clone Pr4R31 was deposited on Mar. 11, 1992 at the Centraalbureau voor Schimmelcultures in Baarn (Holland), according to the conditions of the Budapest Treaty, under number CBS 182.92.

Example 3

Preparation of microorganisms that are specific producers of ostreogricin A and B from *S.ostreogriseus* strain ATCC 27455.

This example comprises a step of mutagenesis on the non-selective microorganism, followed by a selection step.

1. Mutagenesis.

The mutagenesis was performed using ethyl methanesulfonate (EMS).

A suspension of spores of the strain ATCC 2745 is taken up in 50 ml of 0.2 M phosphate buffer pH 7 (0.2 M K2HPO4; pH adjusted to 7 with 0.2 M KH2PO4 solution). This solution is then distributed in 5 100-ml Erlenmeyers in the proportion of 10 ml per Erlenmeyer, equivalent to approximately $9.3 \times 10^8$ spores/Erlenmeyer. EMS is then added into each Erlenmeyer at variable concentrations (see table), and the suspensions are stirred at 280 rpm and 30° C. for 150 or 180 minutes. The suspensions are then transferred and treated as in Example 2 point 1.1. The results obtained are presented in the following table.

| Parameters | Q01 | Q02 | Q03 | Q06 | Q07 |
|---|---|---|---|---|---|
| EMS | 0 | 4% | 4% | 5% | 6% |
| Stirring time | 150 min | 150 min | 180 min | 180 min | 180 min |
| % Survival | 100 | 15.6 | 4.4 | 2.9 | 0.13 |
| % of auxotrophs | 0 | 2.8 | 3.3 | 2.3 | 4.3 |
| Heterogeneity | +/− | + | ++ | +++ | +++ |

2. Selection of producers that are specific for ostreogrycin A.

The selection is performed as in Example 1 in two steps (test of sensitivity to a microbe in a solid medium, and validation in a liquid medium by chromatographic analysis) from the colonies obtained by EMS mutagenesis (QO3 and QO6). Of 1800 clones of each mutagenic treatment (3600 clones in all), 4 were identified in a solid medium (2 for each treatment). 2 strains were confirmed in a liquid medium, under the same conditions as in Example 1, as specific producers of ostreogrycin type A. The clone Pr4QO63 was deposited on 27.01.93 at the Centraal Bureau voor Schimmelcultures in Baarn (Holland), according to the conditions of the Budapest Treaty, under number CBS 143.93.

3. Selection of the specific producers of ostreogrycin B.

The selection is performed as in Example 1 in two steps (test of sensitivity to a microbe in a solid medium, and validation in a liquid medium by chromatographic analysis) from the colonies obtained by EMS mutagenesis (QO3). Of 1800 initial clones, only 1 clone was identified in a solid medium, which was confirmed in a liquid medium. This clone, a specific producer of ostreogrycin type B, designated Pr4QO31, was deposited on 27.01.93 at the Centraalbureau voor Schimmelcultures in Baarn (Holland), according to the conditions of the Budapest Treaty, under number CBS 142.93.

Example 4

Preparation of microorganisms that are specific Producers of virginiamycin A and B from *S.virginiae strain ATCC* 13161.

This example comprises a step of mutagenesis on the non-selective microorganism, followed by a selection step.

1. Mutagenesis.

The mutagenesis was performed using ethyl methanesulphonate (EMS), as in Example 3, on a suspension of spores distributed in 5 100-ml Erlenmeyers in the proportion of 10 ml per Erlenmeyer, equivalent to approximately $3.2 \times 10^9$ spores/Erlenmeyer. The conditions of the mutagenesis and the results obtained are correlated in the following table. The protocol described in Example 3 was followed.

| Parameters | QV4 | QV5 | QV6 | QV9 | QV7 | QV10 |
|---|---|---|---|---|---|---|
| EMS | 0 | 0.5% | 1% | 1.5% | 2% | 3% |
| Stirring time | 100 min | 100 min | 100 min | 100 min | 100 min | 100 min |
| % Survival | 100 | 72 | 55 | 25 | 10 | 0.7 |
| % of auxotrophs | <0.4 | 0.7 | 8.3 | 4.6 | 4.2 | 3.1 |
| Heterogeneity | +/− | +/− | +/− | ++ | + | ++ |

2. Selection of the specific producers of virginiamycin VM.

The selection is performed as in Example 1 in two steps (test of sensitivity to a microbe in a solid medium, and validation in a liquid medium by chromatographic analysis) from the colonies obtained by EMS mutagenesis (QV9 and QV7). Of 1800 clones of each mutagenic treatment (3600 clones in all), 2 were identified in a solid medium according to the protocol described in Example 1 point 1.2 (using $10^7$ sp/l of Streptococcus B96). These 2 strains were confirmed in a liquid medium, under the conditions of Example 1, as specific producers of virginiamycin type VM. The clone Pr4QV71 was deposited on 27.01.93 at the Centraalbureau voor Schimmelcultures in Baarn (Holland), according to the conditions of the Budapest Treaty, under number CBS 140.93.

For the selection in a liquid medium, however, the protocol of Example 1 point 2 was followed, using the following media as inoculum medium and as production medium:

Inoculum medium: Atomised corn steep 20 g; soya bean meal 10 g; yeast antolysate 5 g; groundnut oil 15 g; anhydrous glucode 40 g; MnSO4 0.01 g; CaCO3 5 g; water qs 1l. The pH is adjusted to 6.80 with sodium hydroxide before introduction of the calcium carbonate.

Production medium: Atomised corn steep 20 g; yeast autolysate 5 g; groundnut oil 10 g; anhydrous glucode 5 g; glycerol 25 g; linseed oil 10 g; CaCO3 5 g; water qs 1l. The pH is adjusted to 6.8 with sodium hydroxide before introduction of the calcium carbonate.

3. Selection of the specific producers of virginiamycin type VS.

The selection is performed as in Example 1 in two steps (test of sensitivity to a microbe in a solid medium, and validation in a liquid medium by chromatographic analysis) from the colonies obtained by EMS mutagenesis (QV9). Of 3700 initial clones, only 1 clone was identified in a solid medium (see protocol Example 1 point 1.1), which was confirmed in a liquid medium (see above for the media). This clone, a specific producer of virginiamycin type VS, designated Pr4QV91, was deposited on 27.01.93 at the Centraalbureau voor Schimmelcultures in Baarn (Holland), according to the conditions of the Budapest Treaty, under number CBS 141.93.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

TABLE 1

| MICROORGANISMS | ANTIBIOTICS |
|---|---|
| FUNGI | |
| Micromonospora sp. | vernamycin |
| STREPTOMYCES | |
| S. alborectus | virginiamycin |
| S. conganensis (ATCC13528) | F1370A,B |
| S. diastaticus | plauracin, streptogramin |
| S. graminofaciens | streptogramin |
| S. griseus (NRRL2426) | viridogrisein |
| S. griseoviridus | griseoviridin |
| S. griseoviridus (FERM P3562) | neoviridogrisein |
| S. lavendulae | etamycin |
| S. loidensis (ATCC11415) | vernamycin |
| S. mitakaensis (ATCC15297) | mikamycin |
| S. olivaceus (ATCC12019) | synergistin |
| S. ostreogriseus (ATCC27455) | ostreogrycin |
| S. pristinaespiralis (ATCC25486) | pristinamycin |
| S. virginiae (ATCC13161) | virginiamycin |
| S. antibioticus H-827 | yakusimycin |
| S. kurssanovii (ATCC15824) | A14725 |
| S. komoroensis 1753-Z3 | 1745-Z3 |
| Nocardiopsis flava (ATCC29533) | madumycin |
| ACTINOMYCES | |
| A. auranticolor (ATCC31011) | plauracin |
| A. azureus (ATCC31157) | plauracin |
| A. daghestanicus | etamycin |
| Actinoplanes sp. | A17002 |
| Actinoplanes sp. (ATCC33002) | A15104 |

What is claimed is:

1. A biologically pure culture of a microorganism of the genus Streptomyces, wherein said microorganism is *S. mitakaensis, S. pristinaespiralis, S. ostreogriseus,* or *S. virginiae,* and wherein said microorganism produces the macrolactone component of an antibiotic of the streptogramin family, but produces no detectable amount of the corresponding depsipeptide component of said antibiotic of the streptogramin family, and wherein said antibiotic of the streptogramin family is mikamycin, pristinamycin, ostreogrycin, or virginiamycin, respectively.

2. A biologically pure culture of a microorganism of the genus Streptomyces, wherein said microorganism is *S. mitakaensis, S. pristinaespiralis, S. ostreogriseus,* or *S. virginiae,* and wherein said microorganism produces the depsipeptide component of an antibiotic of the streptogramin family, but produces no detectable amount of the corresponding macrolactone component of said antibiotic of the streptogramin family, and wherein said antibiotic of the streptogramin family is mikamycin, pristinamycin, ostreogrycin, or virginiamycin, respectively.

3. A strain selected from the group consisting of

*S. pristinaespiralis* CBS 182.92;

*S. pristinaespiralis* CBS 183.92;

*S. ostreogriseus* CBS 142.93;

*S. ostreogriseus* CBS 143.93;

*S. virginiae* CBS 140.93; and

*S. virginiae* CBS 141.93.

4. A method for preparing a macrolactone component of an antibiotic of the streptogramin family comprising culturing a microorganism, wherein the microorganism is *S. mitakaensis, S. pristinaespiralis, S. ostreogriseus,* or *S. virginiae,* under conditions effective for the production of said macrolactone component, and recovering the macrolactone component produced, wherein said microorganism produces the macrolactone component of an antibiotic of the streptogramin family, but produces no detectable amount of the corresponding depsipeptide component of said antibiotic of the streptogramin family, and wherein said antibiotic of the streptogramin family is mikamycin, pristinamycin, ostreogrycin, or virginiamycin, respectively.

5. A method for preparing a depsipeptide component of an antibiotic of the streptogramin family comprising culturing a microorganism, wherein said microorganism is *S. mitakaensis, S. pristinaespiralis, S. ostreogriseus,* or *S. virginiae,* under conditions effective for the production of said depsipeptide component, and recovering the depsipeptide component produced, wherein said microorganism produces the depsipeptide component of an antibiotic of the streptogramin family, but produces no detectable amount of the corresponding macrolactone component of said antibiotic of the streptogramin family, and wherein said antibiotic of the streptogramin family is mikamycin, pristinamycin, ostreogrycin, or virginiamycin, respectively.

* * * * *